US00PP15547P2

(12) United States Plant Patent
Doyle et al.

(10) Patent No.: US PP15,547 P2
(45) Date of Patent: Feb. 8, 2005

(54) PRUNE TREE NAMED 'D6N-72'

(50) Latin Name: *Prunus domestica*
Varietal Denomination: D6N-72

(75) Inventors: James F. Doyle, Clovis, CA (US); Carolyn J. DeBuse, Davis, CA (US); Theodore M. DeJong, Davis, CA (US)

(73) Assignee: University of California, Oakland, CA (US)

( * ) Notice: Subject to any disclaimer, the term of this patent is extended or adjusted under 35 U.S.C. 154(b) by 0 days.

(21) Appl. No.: 10/685,876

(22) Filed: Oct. 14, 2003

(51) Int. Cl.[7] ..... A01H 5/00
(52) U.S. Cl. ..... Plt./185
(58) Field of Search ..... Plt./185

*Primary Examiner*—Bruce R. Campell
*Assistant Examiner*—S B McCormick-Ewoldt
(74) *Attorney, Agent, or Firm*—Morrison & Foerster LLP

(57) ABSTRACT

A new prune cultivar designated 'D6N-72' has been developed. The new cultivar is the result of a cross between 'Improved French' and 'Tulare Giant.' The fruit of this cultivar are large, light purple to light bluish purple in color and covered with a grayish waxy bloom. The 'D6N-72' tree is productive and a regular bearer.

2 Drawing Sheets

FIELD OF THE INVENTION

Botanical/commercial classification: (*Prunus domestica*)/ "French-type" prune variety.

Varietal denomination: cv. D6N-72.

BACKGROUND OF THE INVENTION

Prunes (dried plums) are a popular food item providing a good source of vitamin C as well as other vitamins and nutrients for consumers. As such, there is a continued need to develop prune trees with increased yield and quality of plums for the production of prunes.

The long term commercial success of "French-type" prunes, both the European 'Prune d'Ente' and Burbank's 'Improved French', suggests that they will be desirable parents for new cultivars. However, there are several problems involved in incorporating these cultivars directly into a breeding program. Relatively few seedlings from these cultivars express substantial maturity spread, a major industry need. Seedlings of "French" origin are often weak in vigor and slow to come into bearing (up to eight years). These unproductive (juvenile) years greatly extend the breeding cycle. In addition, most seedlings solely derived from this parentage do not attain the level of production of the parent and have a wide range of variability in adaptation to climatic conditions. Even the best selections from France are generally not adapted to California climatic conditions.

Thus there is a tremendous need for developing new prune varieties utilizing "French-type" prune trees in breeding where the resulting trees that express precocity of bearing (shortened juvenility), spread of maturity (both early and late), freedom from heat damage (in both fruit and tree) and vigorous seedling growth.

SUMMARY OF THE INVENTION

In order to meet these needs, the present invention is directed to the 'D6N-72' prune tree which is a new prune cultivar developed for the dried fruit market. It is of the plum species *Prunus domestica*. This new cultivar is the result of a controlled cross made between the European plum/prune cultivars 'Improved French' and 'Tulare Giant' in March of 1992. The cross was made between the prune cultivar 'Improved French' used as the female (seed) parent and the plum cultivar 'Tulare Giant' used as the male (pollen) parent. 'Tulare Giant' is the subject of U.S. Plant Pat. No. 12,224. 'Improved French' is not patented in the United States. Hybrid seed harvested from this cross at the end of the 1992 growing season was given the family designation "P93.22" at planting time in spring of 1993. This family of seedlings, along with many others, was grown into small trees in a nursery at University of California (UC), Kearney Agricultural Center at Parlier, Calif. (KAC) during 1993 and 1994. The trees were dug from the nursery at Kearney at the end of the 1994 growing season and transplanted into a permanent seedling block at University of California, Davis in spring of 1995 (Mar. 1, 1995). The seedling block was located within the Pomology field research area at University of California, Davis and was given the designation of "D Block".

The 'D6N-72' prune cultivar first fruited on the original seedling in July of 1997. The first propagation of selection 'D6N-72' occurred in 1998 in the prune selection block at the KAC. The KAC propagations involved grafting onto two trees of six-year old 'Marianna' plum rootstock (not patented). A second propagation of a single tree of 'D6N-72' was made in 1998 in a prune selection block at the UC Wolfskill Experimental Orchard located near Winters, Calif. The propagation at Wolfskill was made on 'Marianna' plum rootstock that was two years old at the time. The trees grafted in 1998 produced fruit in 2000, attesting to the high degree of precocity of this new cultivar. The first commercial crop of fruit was produced on the propagated trees at Kearney during the 2001 growing season. The fruit produced on the propagated trees has been similar in all aspects to that produced on the original seedling. The original propagules grafted in 1998 continued to produce good commercial crops in 2002 and 2003. The propagules are identical to the original plant in all distinguishing characteristics so as to establish that the claimed plant is stable.

In addition to the 'Marianna' plum rootstock, the new cultivar has also been propagated onto 'Myrobalan' plum rootstock (not patented). Both plum stocks have produced vigorous, healthy and productive trees. Grower test sites were developed for this selection, beginning in 2001 and thereafter, both in the Sacramento and San Joaquin Valleys of California. Field test evaluations have been successful and indicate substantial commercial potential for the new variety.

In comparison with the seed parent 'Improved French', which is the industry standard, 'D6N-72' flowers approximately two weeks earlier. Additionally, the date of fruit maturity for 'D6N-72' in a normal year is early August, approximately 13 days ahead of 'Improved French'. The fruit is large, light purple to light-bluish purple in color and covered with a grayish waxy bloom. The fruit is oval in shape. In early tests, the fruit was substantially larger than 'Improved French' at full maturity. For the French Prune, individual fruit weight ranges from 23.0 to 35.0 grams, whereas 'D6N-72' fruit ranges from 35.0 to 47.0 grams, depending on the crop load on the tree. The fruit stone is nearly free and pits easily.

The 'D6N-72' tree is slightly more vigorous than 'Improved French', it is productive and is a regular bearer. The 'D6N-72' prune has been successfully propagated on 'Marianna' plum rootstock with good results, however it is not recommended that it be grafted on peach rootstocks without significant pre-testing as many other *Prunus domestica* cultivars are incompatible with peach. Fruit of the 'D6N-72' cultivar dries into a very high quality prune with an excellent, fruity flavor. Fresh fruit quality is also excellent with relatively low acidity. For optimum quality fresh fruit should not be picked with less than 19 degrees Brix.

In comparison with the pollen parent 'Tulare Giant', 'D6N-72' flowers at about the same time, however, it produces a fruit much more suited to drying than does the pollen parent 'Tulare Giant,' which is a fresh style market prune. 'D6N-72' is also self-fertile, while 'Tulare Giant' needs a pollinator. Additionally, the fruit of 'D6N-72' is smaller than 'Tulare Giant.' For 'D6N-72,' individual fruit weight ranges from 35.0 to 47.0 grams, whereas for 'Tulare Giant,' fruit weight ranges from 44.0 to 78.0 grams, depending on the crop load on the tree. The fruit of 'D6N-72' is also lighter in color and matures at least one week later than 'Tulare Giant.'

BRIEF DESCRIPTION OF THE DRAWINGS

FIG. 1 shows 'D6N-72' fruit samples. Side and top views of the fruit are shown. In addition, views of sliced fruit and an isolated pit are shown.

FIG. 2 shows branches of 'D6N-72' trees with and without fruit. Sliced and whole fruit samples are also shown.

BOTANICAL DESCRIPTION OF THE PLANT

The following horticultural description was prepared from plant material and fruit obtained from a pair of six-year old grafted trees of the subject new cultivar located at the University of California Kearney Agricultural Center (KAC), 9240 S. Riverbend Avenue, Parlier, Fresno County, Calif. 93648 USA. The plant material was observed during the 2002 and 2003 growing seasons. Descriptions are provided below. Color definitions used in this description are from "The Royal Horticultural Society Colour Chart," 3$^{rd}$ edition, published in 1995.

Tree

The genus and species of the subject new cultivar is *Prunus domestica*. This species is popularly known as "European plum." Individual cultivars of this plum species that are high in sugar content and can dry without fermentation have historically been designated as "prunes." Current nomenclature within the industry now refers to this type of high-sugar plum as a "dried plum" or a prune. The tree of the subject new cultivar is above average in vigor and hardy under normal San Joaquin Valley, Calif. climatic conditions. Tree form is upright to upright-spreading. At the end of the 2002 growing season, the subject trees were pruned to a height of approximately 3.7 meters, with approximately 1.5 to 2.1 meters of growth removed at the time of pruning. Tree width across the crown of the tree is approximately 4.3 meters. The trees have been maintained by pruning in an open-vase training system. The subject trees were propagated on 'Marianna' plum rootstock. Scions of the 'D6N-72' cultivar, obtained from the original seedling at University of California Davis, were placed on the 'Marianna' at Kearney in spring of 1998. A small crop of fruit was produced on the grafted tree in the 2000 growing season, with the first full crop produced in 2001. Fruit produced on the propagated trees was identical to the fruit produced on the original seedling in all aspects. Tree spacing at the Kearney test orchard is 5.49 meters (18 feet) between the rows by 4.88 meters (16 feet) down the row. The new cultivar has been very productive, precocious and a regular bearer.

Trunk

The lower portion of the trunk of the subject trees is made up of the 'Marianna' rootstock. At 20 cm above the surface of the ground, the stock varies from 19.5 to 20.0 cm in diameter. The varietal top is grafted onto the stock at a height ranging from 50.9 to 60.6 cm above the surface of the ground. From 4 to 6 scaffolds arise from the level of the multiple graft union. These primary scaffolds range from 7.5 to 14.0 cm in diameter at the base of the scaffold. The bark surface of the scaffolds is moderately smooth except for the roughened surfaces of the numerous bark lenticels. Bark color is grayish (Fan #4, Sheet 201-B). The bark lenticels are roughly oval in shape and flattened horizontally. Lenticel width ranges from approximately 2 to 7 mm, with occasional lenticels even wider. Lenticel height varies from 1.5 to 3.0 mm. The lenticel surface is roughened and calloused. Color of the lenticel surface callous tissue is a light brown-tan (Fan #4, Sheet 164-B).

Branches

The tree branches are average to slightly above average in thickness for the species. The surface of 2-year-old and older branches is glabrous. Bark lenticels are relatively numerous over the surface of these older branches, causing some roughening of the branch surface. A moderate amount of scarfskin can be present. The color of 2-year-old and older branches is a medium grey (Fan #4, Sheet 201-C). Surface texture of current season's shoots is quite smooth and glabrous. The color of these young shoots is a pale to medium green (Fan #3, Sheet 138-C and Fan #3, Sheet 138-B). Color becomes more brownish as the shoot matures (Fan #4, Sheet 177-A, Fan #4 Sheet 200C, Fan #4 Sheet 200D and Fan #4, Sheet 200-B). Young shoots exposed to sunlight can exhibit shades of red and violet (Fan #2, Sheet 59-C and Fan #4, Sheet 187-A). Shoot internode length is normal for the species, ranging from 20 to 36 mm in length on fruiting hanger branches measured from node to node. The color of new expanding shoot tips is a medium green (Fan #3, Sheet 146-C), with bronze coloration overlying the green in some locations (Fan #4, Sheet 163-A).

Leaves

General leaf size is medium to large. Measurements have been taken from leaves growing on vigorous, upright, current season's shoots. Leaf length ranges from 10.4 to 14.1 cm and leaf width from 4.7 to 6.3 cm. Leaf thickness is average. Leaf surfaces are slightly rugose.

Leaf Form

Leaf form is variable, from oval to slightly obovate. Leaf apex form is acute, but at times only slightly so. The leaf apex is often twisted sideways. Leaves on spurs and small shoots are smaller and more variable in form, ranging from fully obovate to nearly lanceolate. The upper surfaces of the leaf are essentially glabrous. On the lower side of the leaf, the interveinal areas are glabrous. Surfaces of the veins are pubescent. The primary mid-vein is heavily pubescent, with an abundance of medium length hairs.

Leaf Color

Color of the upper leaf surface is dark green (Fan #3, Sheet 137-A). Color of the lower leaf surface is a grey-green (Fan #3, Sheet 138-B). Color of the primary mid-vein on the under side of the leaf is a pale green (Fan #3, Sheet 147-D).

Leaf Margins

Leaf margin form is crenate. The crenations are large and somewhat irregular. The leaf margins are moderately undulate.

Leaf Petiole

The leaf petiole is of average size. Petiole length is rather variable, from 14 to 25 mm. Petiole thickness ranges from 1.0 to 1.5 mm, measured at mid-petiole. Color of the petiole is a pale green (Fan #3, Sheet 147-D). Some petioles are slightly darker green, especially in the petiole groove area (Fan #3, Sheet 148-C). Petiole surfaces are pubescent, more highly so within the petiole groove and along the two ridges subtending the petiole groove.

Leaf Glands

The leaf glands are small and variable, most frequently globose but at times weakly reniform. Diameter of the glands can range from 0.5 to 1.5 mm. Glands usually do not occur on the leaf petiole itself but rather are present on short stalks along the very base of the leaf margins. Glands are variable in number from none to 2, most frequently 2. Gland position is alternate. Color of the young glands is a yellow-green (Fan #3, Sheet 144-C), with the glands becoming darker in color and deteriorating with age.

Leaf Stipules

The leaf stipules are medium to large in size, from 6 to 10 mm at the base of the larger leaves and ranging from 1.5 to 3.0 mm in width. Stipule form is usually linear lanceolate. Occasionally 1 or 2 lobes can be present arising from the basal area of the stipule. These lobes can range from 1.5 to 4.0 mm in length and are also linear lanceolate in form. Stipule margins are serrate and often cupped inwards. Color of the stipules is a light green (Fan #3, Sheet 138-C). Substantial numbers of stipules are persistent throughout the growing season.

FRUIT DESCRIPTION

Maturity

The fruit of the new cultivar is described at full commercial maturity. Date of harvest in 2002 at the University of California Kearney Agricultural Center, Parlier, Fresno County, Calif. was Aug. 8 approximately 13 days ahead of the common prune cultivar 'Improved French' which was harvested in the same location on Aug. 21 in 2002. At that time, fruit of the 'D6N-72' had an average flesh pressure of 4.0 pounds and an average soluble solids content of 20.4 degrees Brix. Harvest was made all at one time as is the common commercial practice in California, where mechanical harvesting by shaker is the norm.

Fruit Size

Fruit size is generally large for a dried plum and quite uniform. Cheek diameter varies from 37 to 45 mm, suture diameter from 36 to 44 mm and axial diameter from 45 to 53 mm.

Fruit Weight

The individual fruit weight ranges from 35.0 to 47.0 grams, depending on the crop load.

Fruit Form

The fruit is most frequently oval in form in lateral aspect, well rounded both apically and basally. In apical aspect, the form varies from globose to slightly oval. The fruit halves can vary from fully symmetrical to slightly asymmetrical.

Fruit Suture

The suture is a thin but distinct line, extending continuously from apex to base. Suture color is usually darker than the surrounding skin surface. Color of the suture is a dark red-purple (Fan #2, Sheet 59-C, Fan #2, Sheet 59B and Fan #2, Sheet 59-A). Most frequently the suture is not depressed, although occasionally, on a few fruit, a slight depression can be observed. No stitching or callousing is present.

Ventral Surface

The ventral surface is usually smooth. Only an occasional fruit displays a slight amount of lipping.

Stem Cavity

The stem cavity is very small. Cavity width varies from 3.0 to 6.0 mm, and cavity length varies from 8.0 to 11.0 mm. The cavity form is oval, tapering somewhat at the ventral suture end. Cavity depth ranges from 3.0 to 4.0 mm.

Fruit Base

The base of the fruit is rounded and regular in form. The base angle is usually at a right angle to the fruit axis.

Fruit Apex

The fruit apex is quite smoothly rounded. Usually there is no depression at the pistil point. The pistil point is apical. A small amount of callous is often present on the pistil point. The callous is tan-brown in color (Fan #4, Sheet 165-B).

Fruit Stem

The fruit stem is of medium length, ranging from 11 to 18 mm. Stem thickness ranges from 1.5 to 1.8 mm, measured at mid-stem. The fruit stem is essentially glabrous, although occasional scattered hairs can be found. Stem color is a pale green at commercial maturity (Fan #3, Sheet 146-D).

Skin

The fruit skin is of average thickness and essentially glabrous. The skin has very slight acidity and is tightly attached to the fruit flesh at commercial maturity. No tendency to crack or split has been observed.

Skin Color

The skin is light purple to light bluish-purple in color at commercial maturity and with the grayish, waxy cuticle bloom intact (Fan #2, Sheet 76-A, Fan #2, Sheet 85A, and Fan #2, Sheet 91-A). With the bloom removed, the skin color is moderately uniform, usually in a washed pattern, and usually from 100 to 95 percent colored. Skin color can be reddish (Fan #4, Sheet 180-A) or darker purple (Fan #4, Sheet 187-A), with various ranges of hues in between. A yellow-amber ground coloration can, at times, be present (up to 5% of the fruit surface). This ground coloration is usually present near the basal end of the fruit or over the basal shoulders (Fan #1, Sheet 23-B). Some yellow speckling is present over the basal shoulders, with the same coloration as the ground color (Fan #1, Sheet 23-B).

Flesh Color

Flesh color can vary from an amber-yellow (Fan #1, Sheet 15-B) to a darker amber-orange Fan #1, Sheet 26-A), with the darker colors in and near the pit cavity. A moderate number of fibers are present throughout the flesh. These flesh fibers are light yellow in color (Fan #1, Sheet 20-A).

Flesh Texture

At commercial maturity, the flesh is firm and relatively fine textured. The flesh becomes soft and juicy with advanced maturity.

Ripening

The fruit ripens evenly.

Flavor

Flavor of the 'D6N-72' fruit is sweet and mild, with a distinctive fruity flavor. The fruit has a relatively low acidity.

Aroma

Aroma is very slight to lacking at commercial maturity.

Eating Quality

Eating quality of the 'D6N-72' fruit is very good, especially when the sugar level reaches or exceeds 19 degrees Brix.

Processing Quality

From early observations and with similar crop loads, the 'D6N-72' cultivar appears to develop larger sized fruit than that of the industry standard dried plum, the 'Improved French'. With similar crop loads, the 'D6N-72' fruit appears to develop comparable sugar levels to those of the 'Improved French'. Fruit of the new cultivar dries into an attractive, high quality dried plum or prune. The fruit stone of the 'D6N-72' is nearly freestone and pits easily using the industry standard "Ashlock" mechanical pitter. The external appearance of the new 'D6N-72' cultivar is similar to that of the 'Improved French' with the possible exception of the 'D6N-72' having somewhat fewer, broader wrinkles. Dried flavor of the 'D6N-72' fruit is lighter than that of the 'Improved French', with a more complex fruity flavor.

STONE DESCRIPTION

Attachment

The stone is nearly free, with a small percentage of fruit having fibers that cling to the stone surface.

Stone Size

The stone is medium in size. Stone length ranges from 28 to 32 mm and stone width ranges from 12 to 15 mm. Thickness of the stone ranges from 7 to 9 mm.

Fibers

A few medium length fibers are attached to the stone surface, primarily along the surfaces of the stone sutures.

Stone Form

The predominant form of the stone is a long narrow oval.

Stone Base

The base of the stone is tapered and slightly truncate. The base angle is variable, from slightly oblique to fully at right angle to the stone axis.

Hilum

The hilum is small in size, from 1.5 to 2.0 mm in length and from 1.0 to 1.5 mm in width. Form of the hilum is oval, but the scar is substantially eroded. Distinct ridges and grooves occur over the neck area of the hilum area, with the ridges converging basally.

Apex

The apex is generally rounded in form, but often with a very low blunt tip. Significant pitting occurs over the apical shoulder along the dorsal edge. A slight amount of erosion can be present, usually laterally, near (or just below) the apex.

Stone Sides

The stone sides are almost always unequal or asymmetrical.

Stone Surface

The stone surfaces are usually relatively smooth laterally, with slightly netted, very low ridging. From 5 to 7 mm up from the stone base, numerous distinct ridges and grooves are present, converging basally. Along the ventral suture from one (to occasionally two) deep grooves are present, varying from continuous to occasionally discontinuous. The groove is usually located from 1 to 2 mm below the edge of the ventral suture (measured at mid-stone), running roughly parallel to the ventral edge but converging both apically and basally.

Ventral Edge

The ventral edge is relatively broad and quite regular. The suture surface can have several shallow grooves and occasionally a low wing can be present.

Dorsal Edge

A single distinct groove is present along the dorsal edge. The groove is quite large from the base of the dorsal edge up to a distance of one quarter to one half of the total length of the dorsal edge, measuring from 1.0 to 1.5 mm in width at mid point. Above this wide groove, on up over the apical shoulder of the dorsal edge, the groove narrows and can, at times become discontinuous. Most frequently the groove at the upper apical edge location appears as only a thin line. A moderate amount of pitting and erosion is present over the apical shoulder of the dorsal edge.

Stone Color

Color of the stone is variable, ranging from a tan color (Fan #4, Sheet 165-C) when dry, to a darker brown (Fan #4, Sheet 165-B) when wet.

Tendency to Split

No tendency for the stone to crack, split or fragment has been observed.

Floral Description

The following floral description was obtained from plant material growing on test trees of the 'D6N-72' cultivar located at the University of California Kearney Agricultural Center, Parlier, Calif. This description was developed during March of both 2002 and 2003. The number of cold chilling hours (total hours below 45 degrees F.) for the 2001 to 2002 winter season at Parlier was 1025 hours. This accumulation is about normal to slightly high. The number of cold hours accumulated for the 2002 to 2003 winter season at Parlier was 813 hours. This represents a relative warm winter.

Because of the similarity of dates of bloom for the 'D6N-72' cultivar in both years, it appears that the chilling requirement of the new 'D6N-72' cultivar was fully satisfied at both levels of chilling.

Flower Buds

Size

The flower buds range from medium to small in size, from 2 to 3 mm in length and from 1.0 to 1.5 mm in width.

Form

General bud form is slightly variable but most frequently conic and plump. The buds most often are moderately appressed to the bearing branch. The flower buds are hardy under the normal climatic conditions that occur in the San Joaquin Valley of Central California.

Color

Bud color is a dark brown (Fan #4, Sheet 200-A).

Bud Surface

The lateral surfaces of the bud scales are essentially glabrous.

Bloom Timing

Bloom timing for the 'D6N-72' cultivar is early for the species. Date of first bloom in 2002 was March 1 with full bloom occurring on Mar. 11 , 2002. Date of first bloom for the 'D6N-72' was Feb. 28 in 2003, followed by full bloom on Mar. 10, 2003. Date of full bloom for the 'Improved French' dried plum cultivar was Mar. 19 in 2003 approximately 9 days after full bloom of the 'D6N-72'. Duration of bloom for the 'D6N-72' can range up to 14 days. Date and duration of bloom for any cultivar can be substantially impacted by the amount of chilling hours received in any specific year and the chilling requirement of the individual cultivar.

Flower Size

Flower size ranges from medium to large for the species. Diameter of the flower, fully expanded, varies from 23 to 27 mm.

Bloom Quantity

The quantity of bloom is abundant. The number of flower buds per node ranges from 1 to 2, most frequently 2.

Flower Petals

Flower petals are medium to large in size. Petals range from 10 to 12 mm in length and from 8 to 10 mm in width. Petal number is five. The petal form is variable, from oval to slightly obovate. Petal color is white (Fan #4, Sheet 155-D). The petal claw is truncate in form and quite short. The claw ranges from 1.0 to 1.5 mm in width, but only averages 0.5 mm in length. The petal margins are moderately undulate and most frequently cupped inwards. Petal apices are variable, with the apex at times smoothly rounded but not infrequently also found with a distinct notch.

Flower Pedicel

Pedicel length ranges from 8 to 12 mm. Pedicel thickness ranges from 1.0 to 1.5 mm measured at mid-pedicel. Color of the pedicel is a yellow-green (Fan #3, Sheet 144-C). The surface of the pedicel is glabrous.

Floral Nectaries

Color of the floral nectaries is a dull orange (Fan #4, Sheet 163-A), lightening with age to a dull yellow-green (Fan #3, Sheet 146-D).

Calyx

Surfaces of the calyx are slightly pubescent, with extremely short and very fine hairs. Calyx color is a dull yellow-green when young (Fan #3, Sheet 152-C), becoming more greenish with age (Fan #3, Sheet 144-C).

Sepals

Sepal surfaces are generally slightly pubescent, with very short and fine hairs, except along the sepal margins where the pubescence is longer and more readily visible. The sepals are of average size, ranging from 4 to 5 mm in length and from 2.5 to 3.5 mm in width. The sepals are most frequently ovate in form. Sepal color is green (Fan #3, Sheet 144-C).

Anthers and Pollen

The anthers are average to slightly above average in size. Anther color is a golden-yellow (Fan #1, Sheet 14-B). Pollen quantity is abundant. Pollen color is yellow (Fan #1, Sheet 13-A). 'D6N-72' is self-fertile. Pollination tests indicate that 'D6N-72' does not need cross-pollination in order to set a commercial crop.

Stamens

The stamens are variable in length, from 7 to 11 mm. The stamens are usually shorter in length than the pistil. Filament color is white (Fan #4, Sheet 155-D).

Pistil

Pistil length ranges in length from 12 to 14 mm, including the ovary. The upper (distil) portion of the style is pale green in color (Fan #3, Sheet 150-D). The basal portion of the style and the ovary are darker green (Fan #3, Sheet 149-D). The surface of the upper portion of the style is glabrous. At times, a few fine hairs can be found on the lower portion of the style and over the upper surface of the ovary.

Disease Resistance

'D6N-72' does not appear to be more or less susceptible to disease than the parent French variety.

DETAILED DESCRIPTION OF THE INVENTION

The breeding strategy of the program to develop the 'D6N-72' can be separated into four distinct phases each having an individual purpose and crossing method. The first phase involved progeny testing of prune cultivars which historically have shown adaptation to California growing conditions. Open pollinated seedling populations derived from each cultivar were screened with the standard fruit evaluation and individuals were identified that expressed precocity of bearing (shortened juvenility), spread of maturity (both early and late), freedom from heat damage (in both fruit and tree) and vigorous seedling growth.

The superior seedlings from Phase 1 were advanced as parents into Phase 2 and Phase 3 hybridization. The purpose of the second phase was to increase the diversity of the germplasm by breeding cultivars that had positive characteristics but had not been used in California production. Superior seedlings possessing commercial cultivar characteristics can be identified at any point in this program. In Phase 3, 'Improved French' is being utilized as a common parent in a "backcross" breeding method. This phase uses superior seedlings identified in Phase 1 and Phase 2 as parents and crosses them to a single common parent, 'Improved French.' This "backcross" breeding method generally produces seedling populations that contain at least 50% "French" genome and have a high potential for producing fruit similar to "French" on vigorous, precocious and productive trees. The fourth phase of the breeding program involves further breeding and selection of the superior seedlings from Phases 2 and 3 for disease and pest resistance.

Pollination and Seedling Cultivation

The annual workings of the breeding program begin at pollination. A pollination list is planned by selecting the parents from the top selected items that show the potential of becoming new cultivars and from the items that have been selected on their breeding potential but lack the potential of becoming cultivars themselves. Flowers from the pollen parent are collected from the trees at the popcorn stage of bloom. The fully closed flowers are removed from the trees and the stamens are separated by rubbing the flowers over a clean screen. The stamens are dried at ambient temperature to release the pollen. The pollen is stored in vials in a refrigerator. Limbs of the seed parents are chosen for crossing when the flowers have reached 40–50% of full bloom. All of the open flowers are removed from the limbs and discarded. The remaining closed flowers are emasculated (petals and stamens are removed) with tweezers, leaving only the pistil and ovary attached to the tree. The collected pollen is placed on each individual pistil of the selected limbs. Five hundred to fifteen hundred flowers are pollinated for each desired cross to ensure a moderately sized progeny family. The large numbers of pollinations are needed because fruit set can be variable due to a variety of factors; poor weather, pollen non-viability, parental incompatibility, and manual damage. The fruits formed by the pollinations are left to mature on the tree until about 10 days before fruit ripening.

Seedling culture is the care of the seedlings from seed to nursery. The first step is the collection of the fruit from the pollinations. The fruit is stored at 32° F. until the time of seed removal. The seed is removed from the fruit in early fall and placed in plastic bags with moist paper towels that contain antibiotics and fungicide. The seed is then stratified for 2 months at 37–45° F. After stratification the seed coats are peeled off each seed to remove any growth inhibitors that might still be present. The peeled seed is planted in cones filled with potting soil. The planted cones are placed in a greenhouse where they germinate under mist. The mist is removed after germination is complete. The seedlings grow in the greenhouse with ample light, heat, and nutrients until their stems have begun to harden and are about 12 inches tall. They are then acclimatized in a lathhouse before being planted in a seedling nursery. At the end of the first growing season, the seedlings are undercut and then planted in high density seedling blocks at the University of California Davis campus research orchards.

Field Testing

Field testing and evaluation of prune selections such as 'D6N-72' are carried out generally at several levels.

Initial testing involves evaluations made in the seedling blocks located at UC Davis and the selections blocks at Kearney, Calif. and Winters, Calif. Initial fruit evaluation is made on the original self-rooted seedlings in the high density seedling blocks. When enough fruit is available on a seedling for preliminary data collection and a positive evaluation has resulted, the seedling becomes a "selection" and is then considered for repropagation in prune selection blocks located at the Kearney Agricultural Center—Parlier, Calif. and at the Wolfskill Experimental Orchard at Winters, Calif. Depending on the perceived potential of the individual selection, from two to four trees of any one selection are established on commercial rootstock. Variations in fruit size, tree vigor, maturity date and other characteristics may, and often do, occur when the selection is moved onto a rootstock from the original seedling. Most individual selections are refruited in the selection blocks prior to advanced testing with growers.

Subsequent testing involves the establishment of advanced selections in grower orchards in various prune growing locations. Again, depending on the perceived value of the individual item, from two to fifty trees of any one selection are established at any one location. Grower tests are established in counties throughout the Sacramento and San Joaquin Valleys in California where prunes are a commercial crop.

Further testing involves the planting of small test acreage, usually of a single targeted selection. The size of these further tests depends on the apparent potential of the individual selection and the level of risk that the cooperating grower wishes to assume. Planting size ranges from twenty five up to several hundred trees. Commercial value of an item can be established in test markets with the expanded production of this further testing.

Selection and Evaluation

Selection and evaluations begin with the first time the seedlings bloom. The tree is noted for precocity and is checked later to see if it successfully set fruit. When a seedling sets its first sizable crop, the fruit is evaluated in the field setting. Maturity date, tree vigor, crop load, fruit size, fruit color, internal flesh quality, pit size, pit type (cling or free), fresh taste, and external flaws are recorded. During this first evaluation, trees can be discarded on the basis of any of these characteristics, except for crop load which is usually only used as a disqualifier after several years of cropping. Some examples of first year disqualifiers are high acidity or astringency, extremely tight pit, large pit size, split pits, gas pockets, lack of firmness in flesh, green or mottled color, small fruit size, deep sutures, cracks on side or ends, heat damage, russet scab, and early fruit drop.

If the field evaluation of a seedling is positive and the fruit quality shows potential, a sample of ten fruit is collected and a secondary fresh evaluation is done in the laboratory. This evaluation is done on the same day as the field evaluation. The fruit is weighed and the average fruit weight (g) is recorded. The maturity of the fruit is estimated by pressure testing the flesh of the ten fruit and recording the average (PSI). The soluble solids are sampled by taking half of each fruit and pulverizing them together in a blender then examining the clear juice with a refractometer. This method establishes the average soluble solids (Brix) of the sample. Again, taste and any exterior or internal flaws are recorded. If the sample shows a high soluble solids compared to other samples at that ripening date and the flavor and fruit quality are above average then a larger sample is collect from the seedling for test drying. If the sample shows low soluble solids or poor fruit quality then the seedling is either marked for discard or evaluation in the next year.

The next step in the evaluation system is to test dry the harvested samples. A dehydrator such as Harvest Saver dehydrator, built by Commercial Dehydrator Systems, Inc., may be utilized to dry the fruit. The samples are placed in net bags and washed before drying. They are dried for two hours at 185° F. after which the temperature is lowered to 165° F. for the remaining time. Samples are dried between 18 to 24 hours depending on filled drier capacity and individual sample characteristics. The prune samples are weighed before and after drying and the fresh to dry ratio is calculated. The dried fruit count per pound is also recorded. The prune samples are stored at 32° F. until the late fall when the final evaluation takes place.

The last evaluation for the year is the rehydrated or processed evaluation. The prune samples are rehydrated by submerging the fruit in water that is between 185–203° F. for six to eight minutes. The rehydrated prunes are placed in a plastic bag and stored in a refrigerator until their moisture content has equalized. The processed dried plums are evaluated. They are evaluated for fruit size, fruit color, color uniformity, surface wrinkles, skin peel, surface brightness, fruit shape, pit size, pit adherence, flesh color, flesh quality, and taste. Taste and appearance play a large role in the advancement of a seedling selection. Items are discarded if any of these traits do not equally compare to or exceed the standards set by the cultivar, 'Improved French'.

The evaluations described above take place at all levels of testing. The emphasis on individual traits changes at each level. In early testing, more emphasis is given to the actual fruit characteristics during the processed evaluation. In later testing the whole tree characteristics are emphasized, such as time of maturity over varying environments, annual bearing habits, crop load, and tree structure.

'D6N-72'

As detailed above, 'D6N-72' ('Improved French'×'Tulare Giant') is a high quality drying plum with a fruity flavor and thick meaty flesh. This new cultivar has been identified utilizing the above described selection and evaluation procedure.

The maturity date of 'D6N-72' falls approximately ten to fifteen days before the industry standard 'Improved French'. The size of the fruit averages 40 grams fresh weight with an average soluble solids between 21.0–24.0 degrees brix. The fruit is an oval shape, without a neck. A purple-rose skin color covers the entire fruit at maturity. The flesh is a golden orange and retains the golden color after drying. The fruit dries without slabing or bleeding and the pit remains semi-free. The results of a pitting trial show that the pit comes free of the flesh and the processed fruit is of high eating quality. The shape of the dried fruit is flatter than "French." The flatness of 'D6N-72' may be due to the drying process and not a fruit quality in itself.

The harvest data of 'D6N-72' in comparison to Sutter and French are shown in Table 1.

TABLE 1

Harvest Data Summary of the Advanced Selections

| Selection | Harvest Date | Days From "French" | Soluble Solids % | Fruit Size (ct/lb) | Crop Load |
|---|---|---|---|---|---|
| 'D6N-72' | Aug. 8, 2002 | −12 days | 23.6 | 36 | Med |
| Sutter (WEO) | Aug. 14, 2002 | −9 days | 30.8 | 39 | Light |
| French (WEO) | Aug. 22, 2002 | 0 days | 28.9 | 35 | Light |

What is claimed is:

1. A new and distinct prune tree, 'D6N-72', substantially as described and illustrated herein.

* * * * *

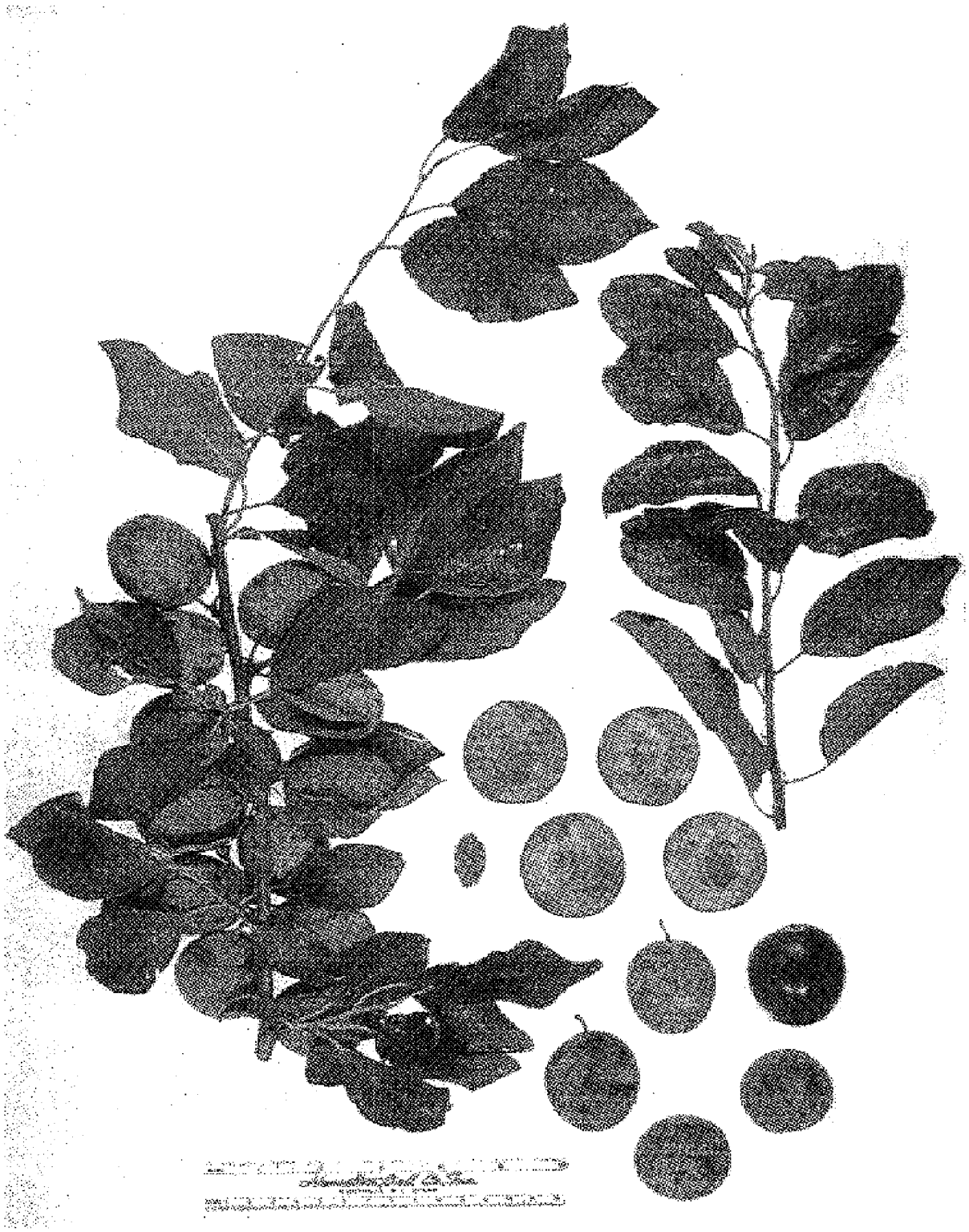

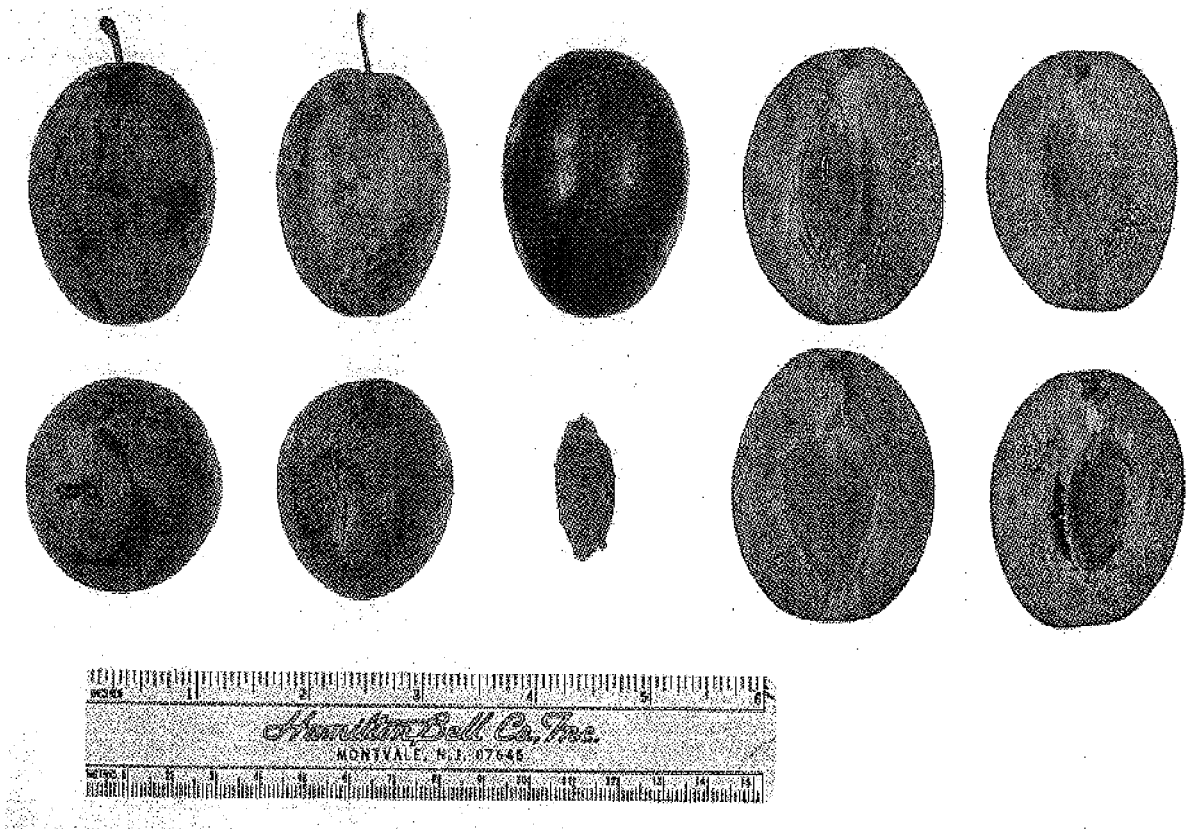
Hamilton Bell Co. Inc.
MONTVALE, N.J. 07645